United States Patent [19]

Cordier

[11] 4,410,739

[45] Oct. 18, 1983

[54] PREPARATION OF META-CHLOROPHENOLS BY SELECTIVE HYDRODECHLORINATION OF POLYCHLOROPHENOLS

[75] Inventor: Georges Cordier, Francheville, France

[73] Assignee: Rhone-Poulenc Industries, Paris, France

[21] Appl. No.: 332,846

[22] Filed: Dec. 21, 1981

[30] Foreign Application Priority Data

Dec. 24, 1980 [FR] France .................. 80 27938

[51] Int. Cl.$^3$ ............................................. C07C 39/24
[52] U.S. Cl. ................................. 568/774; 568/716; 568/744; 568/746
[58] Field of Search ............... 568/774, 745, 746, 799, 568/716

[56] References Cited

U.S. PATENT DOCUMENTS

| | | | |
|---|---|---|---|
| 2,803,669 | 8/1957 | Brainerd | 568/774 |
| 3,912,782 | 10/1975 | Kiel et al. | 568/774 |
| 3,912,783 | 10/1975 | Wedemeyer et al. | 568/774 |
| 4,060,562 | 11/1977 | Wedemeyer et al. | 568/774 |

*Primary Examiner*—Werren B. Lone
*Attorney, Agent, or Firm*—Burns, Doane, Swecker & Mathis

[57] ABSTRACT

Meta-chlorophenols useful as intermediates in various organic syntheses are prepared by selectively catalytically hydrodechlorinating a polychlorophenol in liquid organic phase and in the presence of a nobel metal catalyst and a Lewis acid, said polychlorophenol bearing chlorine substituents in both the meta- and ortho- and/or para-positions.

24 Claims, No Drawings

PREPARATION OF META-CHLOROPHENOLS BY SELECTIVE HYDRODECHLORINATION OF POLYCHLOROPHENOLS

CROSS-REFERENCE TO RELATED APPLICATIONS

My copending applications, Ser. No. 332,740 and Ser. No. 332,833, both filed concurrently herewith; and both assigned to the assignee hereof.

BACKGROUND OF THE INVENTION

1. Field of the Invention

The present invention relates to the preparation of phenols containing a nuclear chlorine substituent in at least one of the meta-positions relative to the phenolic hydroxyl function, and, more especially, to the preparation of such meta-chlorophenols via the hydrodechlorination of the more highly chlorinated chlorophenols.

As utilized and intended herein, the expression "meta-chlorophenols" will hereafter connote phenols bearing a chlorine atom substituent in at least one of the meta-positions.

The meta-chlorophenols, and in particular 3-chlorophenol and 3,5-dichlorophenol, are compounds which are of very great industrial value as intermediates in various organic syntheses.

2. Description of the Prior Art

A plurality of methods for the preparation of the meta-chlorophenols have heretofore been proposed to this art. Methods for generating the phenol group in chlorine-substituted aromatic compounds (for example, by alkaline hydrolysis of polychlorobenzenes, or by nitration of 3-chlorobenzene and 3,5-dichlorobenzene, followed by the reduction of the nitro group to an amino group, the diazotization of the latter and ultimate decomposition of the diazonium salt), methods for chlorinating polychlorophenols are particularly exemplary. The latter method is of very great industrial value because of the availability of the polychlorophenols, certain of which are conventional compounds, while others are by-products of limited value, which it is important to utilize.

Thus, for example, isomeric trichlorophenols and tetrachlorophenols, some of which contain one or two chlorine atoms in the meta-position relative to the phenolic hydroxyl, are obtained during the preparation of 2,3,4,6-tetrachlorophenol and pentachlorophenol by chlorinating 2,6-dichlorophenol, which is a by-product from the preparation of 2,4-dichlorophenol. These various polychlorophenols constitute preferred starting materials for the preparation of meta-chlorophenols by dechlorination. One method for removing the excess chlorine atoms consists of subjecting the polychlorophenols to hydrogenation in the vapor phase or in the liquid phase, in the presence of a catalyst. For reasons of simplicity, the expression "hydrodechlorination" will hereafter connote the dechlorination of polychlorophenols by hydrogenation.

The crux of the problem presented by the hydrodechlorination of polychlorophenols to yield 3-chlorophenol or 3,5-dichlorophenol is the selective removal of the chlorine atoms in the 2- and/or 4- and/or 6-positions relative to the phenolic hydroxyl. Various processes for the hydrodechlorination of polychlorophenols have been proposed, but a data none has proved fully satisfactory.

Thus, U.S. Pat. No. 2,803,669 features a process for the hydrodechlorination of polychlorophenols in the vapor phase, by passing a gaseous mixture of hydrogen and polychlorophenols over a catalyst based on cuprous halides (for example, cuprous chloride) deposited on alumina, the catalyst being maintained at highly elevated temperature (350° to 550° C.). When applied to the hydrodechlorination of 2,3,4,6-tetrachlorophenol, this process does not permit of the selective removal of the chlorine atoms in the 2-, 4- and 6-positions relative to the phenolic hydroxyl function. Indeed, the reaction mixture resulting from the hydrogenation essentially consists of 2,4-dichlorophenol and 2,6-dichlorophenol.

And French Patent Application No. 73/43,484, published under No. 2,209,738, proposes a process for the preparation of meta-halogenophenols by dehalogenating polyhalogenophenols by hydrogenation in the liquid phase at an elevated temperature, in the presence of a catalyst comprising either one or more sulfides or polysulfides of iron, nickel or cobalt, or a noble metal, such as palladium or platinum, associated with a sulfur derivative. The reaction is preferably carried out in the presence of a base, such as alkali metal hydroxides or carbonates, in order to neutralize the hydracids generated by the reaction, as they are formed. Although this process is shown to be very selective with respect to the formation of meta-chlorophenols, it displays the distinct disadvantage in that it must be carried out in the the presence of a base, and in particular an alkali metal base, under temperatures (the temperature must preferably be between 180° and 330° C.) which favor the formation of halogenodioxins, and in particular of polychlorodioxins, certain of which are known to be highly toxic. In practice, a disadvantage of this type renders the process devoid of any meaningful industrial value. Thus, serious need exists in this art for a selective process for obtaining meta-chlorophenols via the hydrodechlorination of polychlorophenols, which process would obviate the need for the presence of alkali metal bases.

SUMMARY OF THE INVENTION

Accordingly, a major object of the present invention is the provision of an improved process for the selective hydrodechlorination of polychlorophenols, which improved process is conspicuously devoid of those disadvantages and drawbacks immediately above outlined.

Briefly, the present invention features a process for selectively preparing chlorophenols bearing a chlorine atom substituent in at least one of the meta-positions relative to the phenolic hydroxyl group, by the hydrogenation, under the influence of heat, in the liquid phase, and in the presence of a catalyst based on a noble metal of Group VIII of the Periodic Table, of polychlorophenols having the structural formula (I):

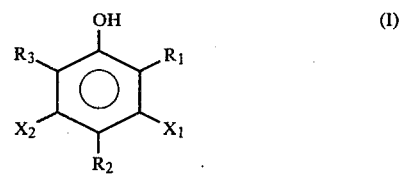

in which: $X_1$ and $X_2$, which are identical or different, each represents a chlorine atom, a hydrogen atom or an alkyl, aryl, arylalkyl, alkoxy or aryloxy radical, at least one of the symbols $X_1$ and $X_2$ representing a chlorine atom, and $R_1$, $R_2$ and $R_3$, which may also be identical or different, each represents a chlorine atom, a hydrogen atom, an alkyl radical, an aryl or arylalkyl radical or an alkoxy or aryloxy radical, at least one of the symbols $R_1$, $R_2$ and $R_3$ representing a chlorine atom, and said hydrodechlorination being characterized in that it is carried out in an organic phase, in the presence of a Lewis acid.

DETAILED DESCRIPTION OF THE INVENTION

More particularly according to this invention, in the formula (I), those radicals $X_1$, $X_2$, $R_1$ and $R_3$ which do not symbolize a chlorine atom represent more advantageously an alkyl radical containing from 1 to 10 carbon atoms and preferably from 1 to 4 carbon atoms, such as methyl, ethyl, n-propyl, isopropyl, n-butyl, isobutyl or t-butyl radicals, a phenyl radical, a benzyl radical, an alkoxy radical containing from 1 to 10 and preferably from 1 to 4 carbon atoms, such as methoxy, ethoxy, n-propoxy, isopropoxy or n-butoxy radicals, or the phenoxy radical.

And consistent with accepted definition, the term "Lewis acid" connotes compounds which accept electron pairs. To carry out the present invention, all types of Lewis acids can be used, in particular those mentioned in the work edited by G. A. Olah and entitled *Friedel-Crafts and Related Reactions*, Volume I, pages 191 to 197 (1963). Among the Lewis acids, it is preferred to use the acidic halides, compare: G. A. Olah, loc. cit., pages 215 to 219, and more particularly the halides of the elements of Groups 3a, 4a, 5a, 1b, 2b, 4b, 5b, 6b, 7b and 8 of the Periodic Table of elements (compare *Handbood of Chemistry and Physics,* edited by R. C. Weast, 53rd edition, 1972–1973), such as the chlorides, bromides, fluorides and iodides of boron, aluminum, tin, phosphorus, arsenic, bismuth, titanium, zirconium, vanadium, molybdenum, iron, cobalt, nickel, copper, zinc and cadmium. Specific examples of these halides which are representative are: aluminum trichloride, aluminum tribromide, aluminum triiodide, stannic and stannous chlorides, stannic and stannous bromides, bismuth trichloride, bismuth tribromide, boron trifluoride and complexes thereof with electron-donating compounds, such as ethers (for example, boron trifluoride diethyl etherate), boron trichloride, boron tribromide, the tetrachlorides of titanium, zirconium and vanadium, molybdenum chlorides, ferric chloride, ferric bromide, cuprous chloride, cupric chloride and zinc chloride. From among the aforementioned halides, it is preferred to use aluminum trichloride and tribromide.

It will of course be appreciated that it is equally possible to use a single Lewis acid or a mixture of several Lewis acids in carrying out the process according to the invention.

The amount of Lewis acid, expressed as the molar ratio Lewis acid/polychlorophenol, can vary over wide limits. Preferably, the amount of Lewis acid is calculated such that the above-mentioned molar ratio is at least $1 \times 10^{-4}$ and preferably at least $1 \times 10^{-2}$. There is no critical upper limit to this ratio, but for obvious practical reasons, it does not need to be more than 2 and preferably no more than 1.

The reaction medium can consist of the polychlorophenol(s) subjected by hydrodechlorination, if they are liquid under the reaction conditions, or of one or more solvents which are inert under the said reaction conditions. Examples of solvents which are exemplary are: aliphatic hydrocarbons such as octane and hexane, cycloaliphatic hydrocarbons such as cyclohexane, aromatic hydrocarbons such as benzene, toluene and xylenes, and chlorohydrocarbons such as chlorobenzene and polychlorobenzenes.

Among these solvents, monochlorobenzene and polychlorobenzenes are of particular value because they permit good dissolution of the chlorophenols and the Lewis acids, in particular aluminum trichloride and tribromide.

It is even more preferable to use dichlorobenzenes and trichlorobenzenes, essentially because of their boiling points.

A valuable embodiment of the process of the invention consists of introducing, into the reaction medium, hydriodic acid, hydrobromic acid or free iodine or bromine, which, in said medium, are reduced by hydrogen to the corresponding hydracids.

Hydriodic acid (or iodine) is preferably used.

The amount of hydracid used is not critical. In general, the molar ratio hydracid (or corresponding halogen equivalent)/polychlorophenol is at least $1 \times 10^{-4}$ and preferably at least $1 \times 10^{-2}$. The upper limit to this ratio is not critical. This ratio can reach a value of 5, but there is generally no need for it to be greater than 2 and preferably no greater than 1.

The presence of hydriodic or hydrobromic acid is of particular value in the hydrodechlorination of polychlorophenols in a polychlorobenzene, because hydrodechlorination of the solvent is readily avoided.

The concentration of polychlorophenol in the solvent employed is not critical.

Because of the sensitivity of Lewis acids and in particular aluminum halides to water, the reaction medium is preferably substantially completely anhydrous.

The nobel metals upon which the catalysts utilized per the invention are based, are mainly metals of Group VIII of the Periodic Table, such as ruthenium, rhodium, palladium, osmium, iridium and platinum. Palladium is the preferred metal. The metal can be in the pure metallic state or in the form of chemical compounds thereof; in general, the metal is preferably used in the metallic form because, under the operating conditions of reaction, compounds tend to be reduced to their metallic state. The catalyst can either be supported or unsupported. Any inert support which is itself known can be used as the catalyst support; more particularly suitable supports which are exemplary are carbon black, silica and barium sulfate; carbon black is a preferred support. The catalyst and its support are advantageously in a finely divided form; specific surface areas of more than 100 m$^2$/g are generally suitable.

The amount of catalyst used is such that the proportion by weight of noble metal of the catalyst, relative to the compound of the formula (I) to be treated, typically ranges from 0.01 to 10% and preferably from 0.1 to 5%.

The reaction temperature typically ranges from 50° to 350° C. and preferably from 100° to 250° C.

The hydrogen partial pressure can also vary over wide limits and be greater than, less than or equal to atmospheric pressure. More specifically, the hydrogen pressure ranges from 0.1 to 60 bars and preferably from 0.5 to 50 bars. Pressures of more than 60 bars could indeed be used, but this does not result in any particular advantages. The total pressure at which the reaction is carried out essentially depends on the temperature conditions, the volatility, under these conditions, of the Lewis acid and any solvent employed, and the degree of the hydrogen partial pressure. It is self-evident that the total pressure must be sufficient to maintain the reaction medium liquid.

Exemplary of the polychlorophenols of the formula (I) which are useful starting materials in the process according to the present invention are: 2,3-dichlorophenol, 2,5-dichlorophenol, 3,4-dichlorophenol, 2,3,4-trichlorophenol, 2,3,6-trichlorophenol, 2,4,5-trichlorophenol, 2,3,5-trichlorophenol, 3,4,5-trichlorophenol, 2,3,4,6-tetrachlorophenol, 2,3,4,5-tetrachlorophenol, 2,3,5,6-tetrachlorophenol, pentachlorophenol, 2,3,4-trichloro-6-methylphenol, 2,3-dichloro-6-methylphenol, 2,3,4,6-tetrachloro-5-methylphenol, 2,3-dichloro-5-methylphenol, 2,3,5,6-tetrachloro-4-methylphenol, 2,5-dichloro-3,4-dimethylphenol, 2,5-dichloro-4-ethylphenol, 2,5-dichloro-4-propylphenol, 2,5-dichloro-4-t-butylphenol, 3,4,6-trichloro-2-benzylphenol, 3,4-dichloro-2-methoxyphenol, 3,6-dichloro-2-methoxyphenol, 4,5-dichloro-2-methoxyphenol, 5,6-dichloro-2-methoxyphenol, 3,4,6-trichloro-2-methoxyphenol, 3,4,5-trichloro-2-methoxyphenol, 3,4,5,6-tetrachloro-2-methoxyphenol, 4,5-dichloro-3-methoxyphenol, 5,6-dichloro-3-methoxyphenol, 2,5-dichloro-3-methoxyphenol, 4,5,6-trichloro-3-methoxyphenol, 2,3,6-trichloro-3-methoxyphenol, 4,5-dichloro-2-phenoxyphenol, 2,3,5,6-tetrachloro-4-phenoxyphenol, 3,4-dichloro-3-ethoxyphenol, 3,4,5-trichloro-2-ethoxyphenol, 3,4-dichloro-2-phenylphenol and 3,5,6-trichloro-2-phenylphenol.

In actual practice, the unsubstituted di-, tri-, tetra- and penta-chlorophenols are preferably used. It is possible, without departing from the scope of the present invention, to subject mixtures of two or more than two of the aforenoted polychlorophenols to hydrodechlorination, it also being possible for these polychlorophenols to comprise minor amounts of polychlorophenols which do not bear chlorine atom substituents in the meta-position.

The following are exemplary of those phenols bearing a chlorine atom substituent in at least one of the meta-positions relative to the phenolic hydroxyl group, which are conveniently prepared by the process according to the present invention: 3-chlorophenol, 3,5-dichlorophenol, 3-chloro-6-methylphenol, 3-chloro-5-methylphenol, 3-chloro-4-methylphenol, 3,5-dichloro-4-methylphenol, 5-chloro-3,4-dimethylphenol, 3,5-dichloro-4-ethylphenol, 3,5-dichloro-4-propylphenol, 3,5-dichloro-4-t-butylphenol, 3-chloro-2-benzylphenol, 3-chloro-2-methoxyphenol, 3-chloro-6-methoxyphenol, 3,5-dichloro-2-methoxyphenol, 3-chloro-5-methoxyphenol, 3-chloro-6-phenoxyphenol, 3,5-dichloro-6-phenoxyphenol, 3-chloro-2-ethoxyphenol and 3-chloro-2-phenylphenol.

The process according to the invention can be carried out either continuously or batchwise. Upon completion of the reaction, the catalyst is filtered off and can be recycled as such into a further hydrodechlorination operation. The metachlorophenols formed can easily be separated from the reaction mixture by simple distillation.

In order to further illustrate the present invention and the advantages thereof, the following specific examples are given, it being understood that same are intended only as illustrative and in nowise limitative.

EXAMPLE 1

The following materials were introduced into a 70 ml tantalum-lined stainless steel autoclave equipped with a stirring system:

(i) 1.332 g of pentachlorophenol ($5.10^{-3}$ mol);
(ii) 0.4 g of a catalyst consisting of palladium deposited on an active charcoal having the specific surface area 1,000 $m^2/g^{-1}$, and containing 5% by weight of palladium metal (namely, 0.02 g of palladium);
(iii) 0.295 g of aluminum tribromide ($1.1.10^{-3}$ mol); and
(iv) 20 ml of cyclohexane.

After the autoclave had been closed, its contents were heated to 190° C., hydrogen was then introduced until the total pressure attained a value of 50 bars, and these conditions were maintained for 4 hours.

The contents of the autoclave were subsequently cooled, degassed and then drawn off. The reaction mixture was then filtered in order to separate off the catalyst, and the latter was washed 3 times with 20 ml of ethanol. The wash alcohol was added to the filtrate, and the organic phase was distilled in order to remove the alcohol and the cyclohexane. 1 g of a residue was collected, in which the chlorophenols were determined and identified by vapor phase chromatography.

The results of the analysis reflected that all of the pentachlorophenol had been converted [degree of conversion (DC): 100%]. The following were identified in the distillation residue:

(1) 3-chlorophenol: yield relative to the pentachlorophenol introduced (RY)=4%;
(2) 3,5-dichlorophenol: RY=96%.

EXAMPLE 2

Example 1 was repeated, but with the pentachlorophenol being replaced by 2,3,4,6-tetrachlorophenol. The reaction time was 6 hours.

The following results were obtained:
DC of tetrachlorophenol=100%;
RY of 3-chlorophenol=96%;
RY of phenol=4%.

EXAMPLE 3

Example 1 was repeated, but with the aluminum tribromide being replaced by 0.6 g of aluminum chloride. The reaction temperature was 180° C. and the total pressure after introducing the hydrogen was 21 bars.

The results obtained were as follows:
DC of pentachlorophenol=100%;
RY of 3-chlorophenol=8%;
RY of 3,5-dichlorophenol=92%.

EXAMPLE 4

Example 1 was repeated, but with 4 g (0.015 mol) of pentachlorophenol, 1 g of aluminum trichloride (0.0075 mol), 0.5 g of a catalyst consisting of Pd deposited on charcoal in a proportion of 5%, and 5 ml of benzene being introduced.

After a reaction time of 8 hours at 190° C. under a total pressure of 40 bars, a degree of conversion of 100% of the pentachlorophenol was obtained and yields of 92% of 3,5-dichlorophenol, 6% of 3-chlorophenol and 2% of phenol were obtained.

EXAMPLE 5

The following materials were introduced, under an anhydrous atmosphere, into a 250 ml stainless steel autoclave equipped with a stirring system:

(i) 10.7 g of pure pentachlorophenol (0.04 mol);
(ii) 1.35 g of anhydrous aluminum trichloride (0.01 mol);

(iii) 0.4 g of catalyst consisting of 5% strength Pd-on-charcoal;

(iv) 15 ml of 1,2,4-trichlorobenzene; and (v) 81 ml of hydrobromic acid ($10^{-3}$ mol).

The autoclave was purged of the air which it contained with nitrogen and then with dry hydrogen.

The reaction mixture was heated to 210° C., hydrogen being fed therein such that the total pressure in the reactor was on the order of 40 bars.

After a reaction time of 7 hours, the following results were obtained (determinations carried out by vapor phase chromatography):

| DC of the pentachlorophenol | 100% |
| RY of 3,5-dichlorophenol | 95.1% |
| RY of 3-chlorophenol | 2.9% |
| RY of 2,3,5-trichlorophenol | 2.0% |

The solvent was not hydrodechlorinated.

EXAMPLE 6

Example 5 was repeated, but with the pure pentachlorophenol being replaced by 10.7 g of industrial-grade pentachlorophenol comprising:

(a) about 75% (by weight) of pentachlorophenol (0.0302 mol);

(b) about 20% (by weight) of 2,3,4,6-tetrachlorophenol (0.0092 mol); and (c) about 5% of by-products from the chlorination of the phenol.

After a reaction time of 6 hours under the conditions of Example 5, the following results were obtained:

DC of the pentachlorophenol and the 2,3,4,6-tetrachlorophenol: 100%.

The yields of the various compounds determined were calculated in % mol/mol, relative to the pentachlorophenol and the tetrachlorophenol introduced:

| RY of 3,5-dichlorophenol | 52.4% |
| RY of 3-chlorophenol | 13.1% |
| RY of 2,3,5,6-tetrachlorophenol | 10.3% |
| RY of 2,3,5-trichlorophenol | 8.9% |
| RY of 2,3,4-trichlorophenol | 2.9% |
| RY of 2,3,6-trichlorophenol | 4.6% |
| RY of 2,5-dichlorophenol and 2,3-dichlorophenol | 3.1% |

The solvent was not hydrodechlorinated.

EXAMPLE 7

Example 5 was repeated, but with the hydrobromic acid being replaced by $10^{-4}$ gram atom of iodine, and 0.6 g of catalyst consisting of 5% strenght Pd-on-charcoal was introduced instead of 0.4 g.

After a reaction time of 5 hours under the conditions of Example 5, the following results were obtained:

| DC of the pentachlorophenol | 96.6% |
| RY of 3,5-dichlorophenol | 67.4% |
| RY of 2,3,4,5-tetrachlorophenol and 2,3,5,6-tetrachlorophenol | 13.4% |
| RY of 2,3,5-trichlorophenol | 13.8% |
| RY of 3-chlorophenol | 0.3%. |

The solvent was not hydrodechlorinated.

EXAMPLE 8

The following materials were introduced, under an anhydrous atmosphere, into the apparatus used in Example 5:

(i) 2.66 g of pentachlorophenol;

(ii) 0.33 g of aluminum trichloride;

(iii) 40 ml of ortho-dichlorobenzene;

(iv) 9.0 g of gaseous hydriodic acid; and (v) 0.2 g of catalyst consisting of 5% strength Pd-on-charcoal.

The reaction was carried out as in Example 5.

After 2 hours at 210° C. under a total pressure of about 40 bars, the following results were obtained:

| DC of the pentachlorophenol | 86.5% |
| RY of 3,5-dichlorophenol | 53.8% |
| RY of 2,3,4,5-tetrachlorophenol and 2,3,5,6-tetrachlorophenol | 16.1% |
| RY of 2,3,5-trichlorophenol | 16.6% |

The solvent was not hydrodechlorinated.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A process for the selective preparation of a meta-chlorophenol, comprising selectively catalytically hydrodechlorinating, with hydrogen, a polychlorophenol having the structural formula (I):

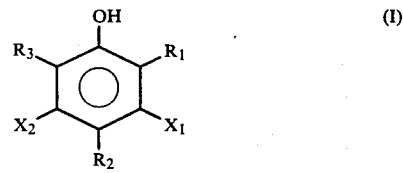

wherein $X_1$ and $X_2$, which may be identical or different, each represents a chlorine atom, a hydrogen atom or an alkyl, aryl, arylalkyl, alkoxy or aryloxy radical, at least one of $X_1$ or $X_2$ being a chlorine atom, and $R_1$, $R_2$ and $R_3$, which may also be identical or different, each represents a chlorine atom, a hydrogen atom, an alkyl, aryl, arylalkyl, alkoxy or aryloxy radical, at least one of $R_1$, $R_2$ or $R_3$ being a chlorine atom, and said selective catalytic hydrodechlorination being carried out at elevated temperatures in liquid organic phase, and in the presence of at least one Lewis acid and a Group VIII noble metal catalyst.

2. The process as defined by claim 1, wherein said polychlorophenol having the structural formula (I) those radicals $X_1$, $X_2$, $R_1$, $R_2$ and $R_3$ which are not a chlorine atom represent an alkyl radical containing from 1 to 10 carbon atoms, a phenyl radical, a benzyl radical, an alkoxy radical containing from 1 to 10 carbon atoms or a phenoxy radical.

3. The process as defined by claims 1 or 2, wherein said at least one Lewis acid comprises a halide of a Group 3a, 4a, 5A, 1b, 2b, 4b, 5b, 6b, 7b or 8 element.

4. The process as defined by claim 3, wherein said at least one Lewis acid comprises an aluminum halide.

5. The process as defined by claim 4, wherein said aluminum halide is aluminum chloride.

6. The process as defined by claim 4, wherein said aluminum halide is aluminum bromide.

7. The process as defined by claim 3, wherein the amount of Lewis acid is such that the molar ratio Lewis acid/polychlorophenol having the structural formula (I) is at least $1.10^{-4}$.

8. The process as defined by claim 7, wherein the amount of Lewis acid is such that the molar ratio Lewis acid/polychlorophenol having the structural formula (I) is at most 2.

9. The process as defined by claim 8, wherein the hydrodechlorination reaction is carried out in the presence of an inert organic solvent.

10. The process as defined by claim 9, wherein said solvent is monochlorobenzene or a polychlorobenzene.

11. The process as defined by claim 10, wherein said solvent is a dichlorobenzene or a trichlorobenzene.

12. The process as defined by claim 9, wherein said solvent is a cycloaliphatic or aromatic hydrocarbon.

13. The process as defined by claim 12, wherein said solvent is cyclohexane or benzene.

14. The process as defined by claim 8, wherein the hydrodechlorination reaction is carried out in the presence of hydriodic acid and/or iodine, or hydrobromic acid and/or bromine.

15. The process as defined by claim 14, wherein the molar ratio hydracid or halogen equivalent/polychlorophenol ranges from $1 \times 10^{-4}$ to 5.

16. The process as defined by claim 8, wherein said catalyst is palladium deposited on an inert support.

17. The process as defined by claim 8, wherein the amount of catalyst, expressed as the weight of noble metal per 100 g of polychlorophenol having the structural formula (I), ranges from 0.01 g to 10 g.

18. The process as defined by claim 8, wherein the hydrodechlorination reaction temperature ranges from 50° to 350° C.

19. The process as defined by claim 18, wherein the hydrogen partial pressure ranges from 0.1 to 60 bars.

20. The process as defined by claim 1, wherein said polychlorophenol having the structural formula (I) is 2,3,4,6-tetrachlorophenol or pentachlorophenol.

21. The process as defined by claim 15, said molar ratio ranging from $1 \times 10^{-2}$ to 1.

22. The process as defined by claim 1, wherein said polychlorophenol having the structural formula (I) is 2,3-dichlorophenol, 2,5-dichlorophenol, 3,4-dichlorophenol, 2,3,4-trichlorophenol, 2,3,6-trichlorophenol, 2,4,5-trichlorophenol, 2,3,5-trichlorophenol, 3,4,5-trichlorophenol, 2,3,4,6-tetrachlorophenol, 2,3,4,5-tetrachlorophenol, 2,3,5,6-tetrachlorophenol, pentachlorophenol, 2,3,4-trichloro-6-methylphenol, 2,3-dichloro-6-methylphenol, 2,3,4,6-tetrachloro-5-methylphenol, 2,3-dichloro-4-methylphenol, 2,3,5,6-tetrachloro-4-methylphenol, 2,5-dichloro-3,4-dimethylphenol, 2,5-dichloro-4-ethylphenol, 2,5-dichloro-4-propylphenol, 2,5-dichloro-4-t-butylphenol, 3,4,6-trichloro-2-benzylphenol, 3,4-dichloro-2-methoxyphenol, 3,6-dichloro-2-methoxyphenol, 4,5-dichloro-2-methoxyphenol, 5,6-dichloro-2-methoxyphenol, 3,4,6-trichloro-2-methoxyphenol, 3,4,5-trichloro-2-methoxyphenol, 3,4,5,6-tetrachloro-2-methoxyphenol, 4,5-dichloro-3-methoxyphenol, 5,6-dichloro-3-methoxyphenol, 2,5-dichloro-3-methoxyphenol, 4,5,6-trichloro-3-methoxyphenol, 2,3,6-trichloro-3-methoxyphenol, 4,5-dichloro-2-phenoxyphenol, 2,3,5,6-tetrachloro-4-phenoxyphenol, 3,4-dichloro-3-ethoxyphenol, 3,4,5-trichloro-2-ethoxyphenol, 3,4-dichloro-2-phenylphenol or 3,5,6-trichloro-2-phenylphenol.

23. The process of claim 1, wherein the Group VIII metal catalyst is in a metallic state.

24. The process of claim 1, wherein the hydrodechlorination reaction temperature ranges from 50° to 350° C., and the hydrogen partial pressure ranges from 0.1 to 60 bars.

* * * * *